US010165996B2

(12) United States Patent
Madhav et al.

(10) Patent No.: US 10,165,996 B2
(45) Date of Patent: Jan. 1, 2019

(54) SYSTEMS AND METHODS FOR DUAL-ENERGY COMPUTED TOMOGRAPHY IMAGING

(71) Applicant: General Electric Company, Schenectady, NY (US)

(72) Inventors: Priti Madhav, Waukesha, WI (US); Uwe Wiedmann, Clifton Park, NY (US); Eric Biehr, Milwaukee, WI (US); Jiahua Fan, Waukesha, WI (US); Jean-Francois Larroux, Buc (FR); Vijay Subramanian, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 331 days.

(21) Appl. No.: 14/871,270

(22) Filed: Sep. 30, 2015

(65) Prior Publication Data
US 2017/0086775 A1 Mar. 30, 2017

(51) Int. Cl.
A61B 6/03 (2006.01)
A61B 6/00 (2006.01)
A61B 6/06 (2006.01)

(52) U.S. Cl.
CPC ............. A61B 6/482 (2013.01); A61B 6/032 (2013.01); A61B 6/06 (2013.01); A61B 6/405 (2013.01); A61B 6/4035 (2013.01); A61B 6/488 (2013.01); A61B 6/542 (2013.01); A61B 6/544 (2013.01); A61B 6/545 (2013.01)

(58) Field of Classification Search
CPC ......... A61B 6/032; A61B 6/405; A61B 6/482; A61B 6/542; A61B 6/544; A61B 6/545

USPC ................... 378/5, 16, 98.9, 98.11
See application file for complete search history.

(56) References Cited

U.S. PATENT DOCUMENTS

| 4,029,963 A | * | 6/1977 | Alvarez | A61B 6/032 378/5 |
| 4,829,551 A | * | 5/1989 | Resnick | H05G 1/66 378/131 |
| 5,400,385 A | * | 3/1995 | Blake | H05G 1/20 323/280 |
| 5,420,781 A | * | 5/1995 | Schmidt | H02M 3/3376 363/132 |

(Continued)

Primary Examiner — Allen C. Ho
(74) Attorney, Agent, or Firm — Dean D. Small; The Small Patent Law Group, LLC

(57) ABSTRACT

An imaging system includes a computed tomography (CT) acquisition unit and a processing unit. The CT acquisition unit includes an X-ray source and a CT detector. The processing unit is configured to determine a voltage delivery configuration for the X-ray source based on at least one of a patient size, a clinical task, or scan parameters. The voltage delivery configuration includes at least one of a transition configuration or a voltage threshold. The transition configuration corresponds to a transition between a high voltage and a low voltage. Portions of acquired data acquired above the voltage threshold are grouped as high energy data and portions acquired below the voltage threshold are grouped as low energy data. The processing unit is also configured to implement the voltage delivery configuration on the CT acquisition unit, and to control the CT acquisition unit to perform an imaging scan using the determined voltage delivery configuration.

25 Claims, 5 Drawing Sheets

(56) References Cited

U.S. PATENT DOCUMENTS

| | | | | |
|---|---|---|---|---|
| 5,602,897 A * | 2/1997 | Kociecki | H05G 1/06 | 378/101 |
| 6,836,529 B2 * | 12/2004 | Li | A61B 6/032 | 378/111 |
| 6,882,703 B2 * | 4/2005 | Price | H01J 35/065 | 378/101 |
| 6,922,462 B2 * | 7/2005 | Acharya | A61B 6/405 | 378/98.11 |
| 7,406,154 B2 * | 7/2008 | Resnick | A61B 6/032 | 378/113 |
| 7,711,082 B2 * | 5/2010 | Fujimoto | A61B 6/032 | 378/115 |
| 7,742,573 B2 * | 6/2010 | Caiafa | H05G 1/58 | 378/101 |
| 7,801,265 B2 * | 9/2010 | Yu | A61B 6/032 | 378/4 |
| 7,813,474 B2 * | 10/2010 | Wu | A61B 6/032 | 378/16 |
| 7,826,587 B1 * | 11/2010 | Langan | A61B 6/032 | 378/16 |
| 7,844,030 B2 * | 11/2010 | Wilson | A61B 6/032 | 378/101 |
| 7,869,561 B2 * | 1/2011 | Dafni | A61B 6/032 | 378/19 |
| 7,949,088 B2 * | 5/2011 | Nishide | A61B 6/032 | 378/16 |
| 7,983,383 B2 * | 7/2011 | Kadomura | A61B 6/032 | 378/16 |
| 8,031,831 B2 * | 10/2011 | Zou | A61B 6/032 | 378/108 |
| 8,050,479 B2 * | 11/2011 | Hsieh | A61B 6/032 | 378/16 |
| 8,155,263 B2 * | 4/2012 | Wu | A61B 6/032 | 378/16 |
| 8,160,206 B2 * | 4/2012 | Wu | A61B 6/032 | 378/4 |
| 8,165,264 B2 * | 4/2012 | Zou | G06T 11/005 | 378/5 |
| 8,194,820 B2 * | 6/2012 | Wang | G01N 23/087 | 378/53 |
| 8,199,875 B2 * | 6/2012 | Chandra | A61B 6/032 | 378/16 |
| 8,311,182 B2 * | 11/2012 | Chandra | A61B 6/03 | 378/5 |
| 8,315,352 B2 * | 11/2012 | Wu | A61B 6/032 | 378/18 |
| 8,320,521 B2 * | 11/2012 | Zou | H01J 35/045 | 378/106 |
| 8,379,797 B2 * | 2/2013 | Abenaim | A61B 6/027 | 378/103 |
| 8,482,949 B2 * | 7/2013 | Bleukx | H02M 7/5387 | 363/132 |
| 8,483,360 B2 * | 7/2013 | Litvin | A61B 6/032 | 378/4 |
| 8,483,361 B2 * | 7/2013 | Sainath | A61B 6/032 | 378/125 |
| 8,520,803 B2 * | 8/2013 | Behling | H01J 35/10 | 378/124 |
| 8,537,965 B2 * | 9/2013 | Dafni | A61B 6/032 | 378/4 |
| 8,548,118 B2 * | 10/2013 | Hsieh | A61B 6/482 | 378/124 |
| 8,588,371 B2 * | 11/2013 | Ogawa | H02M 7/53871 | 378/101 |
| 8,693,638 B2 * | 4/2014 | Dafni | A61B 6/032 | 378/124 |
| 8,712,015 B2 * | 4/2014 | Caiafa | H01J 35/18 | 378/110 |
| 8,755,488 B2 * | 6/2014 | Levene | A61B 6/032 | 378/111 |
| 8,861,681 B2 * | 10/2014 | Caiafa | H02M 3/337 | 378/101 |
| 8,941,076 B2 * | 1/2015 | Abraham | G01T 1/171 | 250/336.1 |
| 8,971,605 B2 * | 3/2015 | Hsieh | G06T 5/005 | 378/21 |
| 9,101,273 B2 * | 8/2015 | Gagnon | A61B 6/032 | |
| 9,149,241 B2 * | 10/2015 | Kim | A61B 6/482 | |
| 9,160,325 B2 * | 10/2015 | Caiafa | H03K 17/04 | |
| 9,204,852 B2 * | 12/2015 | Edic | A61B 6/482 | |
| 9,247,919 B2 * | 2/2016 | Goshen | G06T 11/005 | |
| 9,310,490 B2 * | 4/2016 | Abraham | G01T 1/17 | |
| 9,354,331 B2 * | 5/2016 | Sagoh | A61B 6/032 | |
| 9,438,120 B2 * | 9/2016 | Caiafa | H02M 3/33507 | |
| 9,517,042 B2 * | 12/2016 | Hsieh | A61B 6/032 | |
| 9,532,759 B2 * | 1/2017 | Taguchi | A61B 6/032 | |
| 9,585,626 B2 * | 3/2017 | Gao | A61B 6/032 | |
| 9,588,239 B2 * | 3/2017 | Abraham | G01T 1/247 | |
| 9,645,260 B2 * | 5/2017 | Abraham | G01T 1/247 | |
| 9,662,078 B2 * | 5/2017 | Berglund | A61B 6/4233 | |
| 9,706,971 B2 * | 7/2017 | Popescu | A61B 6/5235 | |
| 9,836,859 B2 * | 12/2017 | Zou | G06T 11/003 | |
| 9,888,894 B2 * | 2/2018 | Wiedmann | A61B 6/482 | |
| 9,952,333 B2 * | 4/2018 | Abraham | G01T 1/17 | |
| 9,964,650 B2 * | 5/2018 | Cho | G01T 1/161 | |

\* cited by examiner

SYSTEMS AND METHODS FOR DUAL-ENERGY COMPUTED TOMOGRAPHY IMAGING

BACKGROUND OF THE INVENTION

The subject matter disclosed herein relates generally to systems and methods for computed tomography (CT) imaging, for example to systems and methods for perfusion studies using CT imaging.

In CT imaging, an X-ray source may be rotated around an object to obtain imaging information. X-rays from the source attenuated by the object may be collected or detected by a detector and used to reconstruct an image. Patient radiation dose from the X-ray source is a concern in clinical practice.

CT imaging may be performed at varying voltage levels of the X-ray source. For example, as part of dual-energy imaging, the X-ray source may be switched between a high voltage and a low voltage during acquisition of imaging information. Conventional systems may experience lower than desired flux at the lower energy or voltage, for example due to power constraints of an X-ray tube. Further, certain dual-energy systems may provide a lower than desired dose coverage or range. Further still, especially for low dose and/or fast rotation time protocols, certain dual-energy systems may provide an energy separation between high and low voltages that is lower than desired.

BRIEF DESCRIPTION OF THE INVENTION

In one embodiment, an imaging system is provided that includes a computed tomography (CT) acquisition unit and a processing unit. The CT acquisition unit includes an X-ray source and a CT detector configured to collect CT imaging data of an object to be imaged. The X-ray source and CT detector are configured to be rotated about the object to be imaged and to collect a series of projections of the object as the X-ray source and CT detector rotate about the object to be imaged. The X-ray source is configured to be switched between a high voltage and a low voltage during collection of the series of projections. The processing unit includes at least one processor operably coupled to the CT acquisition unit. The processing unit is configured to determine a voltage delivery configuration (e.g., waveform configuration) for the X-ray source based on at least one of a patient size, a clinical task, or desired scan parameters. The voltage delivery configuration includes at least one of a transition configuration (e.g., transition time configuration) or a voltage threshold. The transition configuration corresponds to a transition between the high voltage and the low voltage of the X-ray source. (As used herein, a transition between high voltage and low voltage may be understood as including at least one of a transition from high voltage to low voltage and a transition from low voltage to high voltage.) Portions of acquired data acquired above the voltage threshold are grouped as high energy data and portions of the acquired data acquired below the voltage threshold are grouped as low energy data. The processing unit is also configured to implement the voltage delivery configuration on the CT acquisition unit, and to control the CT acquisition unit to perform an imaging scan using the determined voltage delivery configuration. It may be noted that in some embodiments, a source spectrum may be modulated using a fast-changing spectral filter, such as a rotating filter wheel, and the voltage delivery configuration may describe operating parameters of the spectral filter.

In another embodiment, a method that includes determining, with at least one processor, a voltage delivery configuration for an X-ray source of a computed tomography (CT) acquisition unit based on at least one of a patient size, a clinical task, or desired scan parameters. The voltage delivery configuration includes at least one of a transition configuration or a voltage threshold. The transition configuration corresponds to a transition between a high voltage and a low voltage of the X-ray source. Portions of acquired data acquired above the voltage threshold are grouped as high energy data and portions of the acquired data acquired below the voltage threshold are grouped as low energy data. The method also includes implementing the voltage delivery configuration on the CT acquisition unit. Also, the method includes controlling the CT acquisition unit to perform an imaging scan using the determined voltage delivery configuration.

In another embodiment, a tangible and non-transitory computer readable medium is provided that includes one or more computer software modules configured to direct one or more processors to determine a voltage delivery configuration for an X-ray source of a computed tomography (CT) acquisition unit based on at least one of a patient size, a clinical task, or desired scan parameters. The voltage delivery configuration includes at least one of a transition configuration or a voltage threshold. The transition configuration corresponds to a transition between a high voltage and a low voltage of the X-ray source. Portions of acquired data acquired above the voltage threshold are grouped as high energy data and portions of the acquired data acquired below the voltage threshold are grouped as low energy data. (It may be noted that in some embodiments, grouping high energy data and low energy data may include binning in more than 2 groups using 2 or more voltage thresholds.) The one or more computer software modules are also configured to direct one or more processors to implement the voltage delivery configuration on the CT acquisition unit, and to control the CT acquisition unit to perform an imaging scan using the determined voltage delivery configuration.

DETAILED DESCRIPTION OF THE INVENTION

Figure 1:
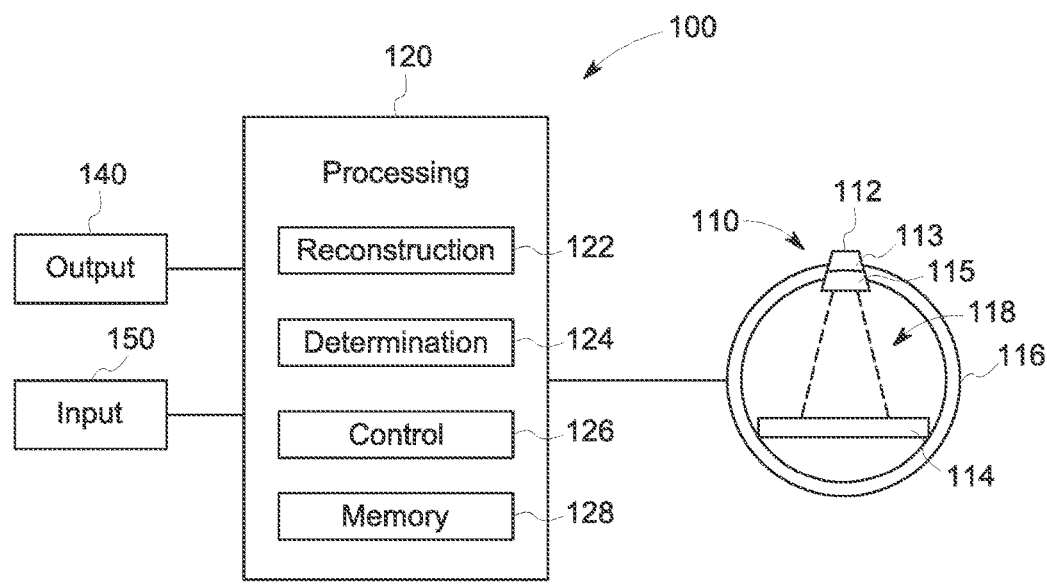
FIG. 1 is a schematic block diagram illustrating an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for improving performance of CT systems using multiple voltages or energies, such as dual-energy spectral imaging systems utilizing an X-ray source that operates at a high voltage and a low voltage. Various embodiments improve flux, energy separation, and/or dose range or coverage. Various embodiments optimize or improve low and high energy stations (and/or waveform configurations) to provide improved imaging performance.

In some dual energy systems, which may be referred to as fast kV switching systems, the high voltage and low voltage may alternate rapidly from view to view during rotation of the X-ray source and detector. In various embodiments, the configuration of high and low energy stations, or configuration of a waveform corresponding to the switching of the voltage, may be implemented and/or adjusted, for example, based on patient anatomy and/or clinical task, to provide improved flux, energy separation, dose coverage, or the like.

For example, a scout scan may be acquired prior to performing an imaging scan. The information from the scout scan may be used to derive the anatomy size and the scan range. Based on the anatomy size, scan range, desired clinical task, and/or system parameters (such as scan field of view (SFOV), rotation time, or collimation, among others), an optimal or improved dual energy scan protocol may be determined and implemented. The dual energy scan protocol may specify, for example, one or more of a kV threshold determining whether information is binned as high or low energy information, and/or the shape of a waveform (including duty cycle, shape of wave transitioning from high to low voltage, and/or shape of wave transitioning from low to high voltage). For example, to diagnose kidney stones, material density accuracy may be important, and high energy separation may be useful in providing improved material density accuracy. Accordingly, the waveform configuration may be adjusted or implemented to provide increased energy separation. As another example, for a relatively large patient, increasing flux may be desirable, and the kV threshold may be increased to provide increased flux.

Various embodiments help overcome challenges in flux, dose, and energy separation between low and high voltages, for example in fast switching applications. By improving or optimizing waveform configurations of waveforms used in fast switching applications, the flux between high and low energies or voltages may be balanced, maximum or improved energy separation may be achieved, and wider dose distribution may be covered. Accordingly, improved dual-energy image quality (e.g., reduction of low signal artifacts, reduction of resolution mismatch, material density accuracy improvement, or the like) may be achieved. Further, the dose may be tailored for a particular patient and/or clinical task.

Various embodiments provide improved imaging. A technical effect of at least one embodiment includes improved flux for dual-energy spectral imaging. A technical effect of at least one embodiment includes improved energy separation for dual-energy scanning A technical effect of at least one embodiment includes improved dose coverage (e.g., ability to perform scan at lower current levels). A technical effect of at least one embodiment includes improved contrast.

FIG. 1 illustrates an imaging system 100 in accordance with an embodiment. The imaging system 100 may be configured, for example, to perform computed tomography (CT) scanning of an object, such as a human or animal patient (or portion thereof), such as CT scanning for a perfusion study. The imaging system 100 includes a CT acquisition unit 110 and a processing unit 120. Generally, the CT acquisition unit 110 is configured to acquire projection data or imaging data (e.g., CT data or CT imaging information), while the processing unit 120 is configured to control the operation of the CT acquisition unit 110, and to reconstruct images using the data acquired by the CT acquisition unit 110. It may be noted that various embodiments may include additional components, or may not include all of the components shown in FIG. 1 (for example, various embodiments may provide sub-systems for use with other sub-systems to provide an imaging system). Further, it may be noted that certain aspects of the imaging system 100 shown as separate blocks in FIG. 1 may be incorporated into a single physical entity, and/or aspects shown as a single block in FIG. 1 may be shared or divided among two or more physical entities.

The depicted CT acquisition unit 110 includes an X-ray source 112 and a CT detector 114. (For additional information regarding example CT systems, see FIG. 8 and related discussion herein.) The X-ray source 112 and the CT detector 114 (along with associated components such as bowtie filters, source collimators, detector collimators, or the like (not shown in FIG. 1)) may rotate about a central axis of a bore of a gantry 116 of the imaging system 100. The depicted X-ray source 112 includes a generator 113 and a tube 115. The generator 113 may be used to control (e.g., via input signals from the processing unit 120) the supply of power to the tube 115 to change the energy level or voltage level of the tube 115. For example, the X-ray source 112 may be utilized to provide varying energy levels during the course of a rotation of the CT acquisition unit 110 around an object to be imaged. In some embodiments, the X-ray source 112 may be configured to be switched between a high voltage (e.g., a nominal 140 kV) and a low voltage (e.g., a nominal 80 kV) as the CT acquisition unit 110 is rotated about an object to be imaged and used to collect a series of projections of the object. In some embodiments, the voltage may be switched from view to view as the CT acquisition unit 110 rotates (e.g., a given view at the high voltage or energy level, the immediately subsequent view at the low voltage or energy level, the next immediately subsequent view at the high voltage or energy level, and so forth).

Generally, X-rays from the X-ray source 112 may be guided to an object to be imaged through a source collimator and bowtie filter. The object to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter module may be configured to absorb radiation from the X-ray source 112 to control distribution of X-rays passed to the object to be imaged.

X-rays that pass through the object to be imaged are attenuated by the object and received by the CT detector 114 (which may have a detector collimator associated therewith), which detects the attenuated X-rays and provides imaging information to the processing unit 120. The processing unit 120 may then reconstruct an image of the scanned portion of the object using the imaging information (or projection information) provided by the CT detector 114. The processing unit 120 may include or be operably coupled to the output unit 140, which in the illustrated embodiment is configured to display an image, for example, an image reconstructed by the processing unit 120 using imaging information from the CT detector 114. The depicted input unit 150 is configured to obtain input corresponding to a scan to be performed, with the processing unit 120 using the input to determine one or more scan settings (e.g., tube voltage, tube current, scanning rotation speed, or the like). The input unit 150 may include a keyboard, mouse, touchscreen or the like to receive input from an operator, and/or may include a port or other connectivity device to receive input from a computer or other source.

In the illustrated embodiment, the X-ray source 112 is configured to rotate about the object. For example, the X-ray source 112 and the CT detector 114 may be positioned about a bore 118 of the gantry 116 and rotated about the object to be imaged. As the X-ray source 112 rotates about the object during an imaging scan, X-rays received by the CT detector 114 during one complete rotation provide a 360 degree view of X-rays that have passed through the object. Other imaging scanning ranges may be used in alternative embodiments. The CT imaging information may be collected as a series of views that together make up a rotation or portion thereof. Each view or projection may have a view duration during which information (e.g., counts) is collected for the particular view. The view duration for a particular view defines a CT information acquisition period for that particular view. For example, each rotation may be made up of about 1000 views or projections, with each view or projection having a duration or length of about 1/1000 of a complete rotation.

As indicated herein, the processing unit 120 is configured to control various aspects of the CT acquisition unit 110 and/or to reconstruct an image using information obtained via the CT acquisition unit 110. For example, the processing unit 120 may be configured to reconstruct a CT image using information collected by the CT acquisition unit 110.

The depicted processing unit 120 is operably coupled to the input unit 150, the output unit 140, and the CT acquisition unit 110. The processing unit 120, for example, may receive information regarding a scan from the input unit 150 that may be utilized in determining a desired clinical task, patient information, and/or scanning parameters to be used for a given imaging scan to be performed with the imaging system 100. As another example, the processing unit 120 may receive imaging data or projection data from the CT detector 114. As one more example, the processing unit 120 may provide control signals to one or more aspects of the CT acquisition unit 110, such as the X-ray source 112 and CT detector 114. The processing unit 120 may include processing circuitry configured to perform one or more tasks, functions, or steps discussed herein. It may be noted that "processing unit" as used herein is not intended to necessarily be limited to a single processor or computer. For example, the processing unit 120 may include multiple processors and/or computers, which may be integrated in a common housing or unit, or which may distributed among various units or housings.

The depicted processing unit 120 is configured to control the CT acquisition unit 110 (e.g., by controlling the activation and deactivation of the X-ray source 112, as well as the energy or voltage level of the X-ray source 112), and to collect CT imaging information during an imaging scan. In various embodiments, the processing unit 120 may control the CT acquisition unit 110 to first obtain a scout projection or scan of an object to be imaged to help determine one or more characteristics of the object (e.g., size, attenuation levels, or the like).

The depicted processing unit 120 is also configured to determine a waveform configuration for the CT acquisition unit 110 (e.g., X-ray source 112) based on at least one of patient size, a clinical task, or desired scan parameters. For example, a patient size and/or information corresponding to attenuation levels of a patient may be determined using a scout scan, information from a database, and/or information entered by an operator. Scan range may also be determined from a scout scan. Similarly, information corresponding to or describing a clinical task may be acquired from a database or from information entered by an operator. The clinical task, for example, may describe the portion of anatomy to be imaged or diagnosed, type and quantity of contrast agent used, type and size of lesion to be evaluated, etc. Scan parameters that may be considered in determining the waveform configuration include scan field of view, or rotation time, collimation, among others. The processing unit 120 may access a look-up table or other resource (e.g., stored in the memory 128) to determine the waveform configuration.

For example, clinical studies and/or historical information may be used to correlate particular waveform configurations that have been demonstrated effective and/or optimal for combinations of patient size, clinical task, and scan parameters.

Figure 2:
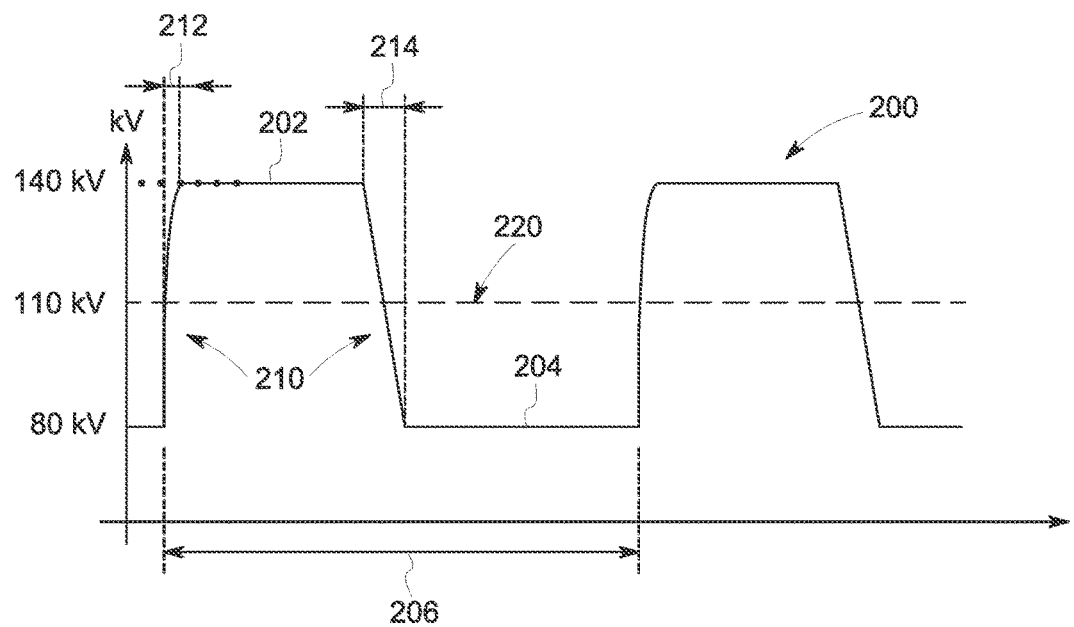
FIG. 2 illustrates an example waveform configuration in accordance with various embodiments.

The waveform configuration, which corresponds to the energy or voltage of the X-ray source 112, includes at least one of a transition configuration or a voltage threshold. As used herein, a kV waveform may be understood as describing the value of a scan kV and its repetition pattern across the kV switching duration. FIG. 2 illustrates an example of a waveform configuration 200 formed in accordance with various embodiments. As seen in FIG. 2, the waveform configuration 200 alternates between a high energy 202 (corresponding to 140 kV) and a low energy 204 (corresponding to 80 kV) over a period 206. It may be noted that alternate or additional energies may be utilized in other waveform configurations. The waveform configuration 200 also includes a transition time configuration 210. In the illustrated embodiment, the transition time configuration 210 includes a rise time 212 and a fall time 214. The rise time 212 corresponds to the time for transitioning from the low energy 204 to the high energy 202, and the fall time 214 corresponds to the time for transition from the high energy 202 to the low energy 204. For example, the fall time 214 may be understood as the time for the voltage to fall from a 90% level to a 10% level between the high energy 202 and low energy 204, and the rise time 212 may be understood as the time for the voltage to rise from a 10% level to a 90% level between the low energy 204 and high energy 202. In the illustrated embodiment, the portion of the waveform configuration 200 corresponding to the rise time 212 and the fall time 214 is generally straight and continuous; however, different slopes or shapes of transition time configurations may be employed in alternate embodiments.

The waveform configuration 200 also includes a voltage threshold 220. The voltage threshold 220 may be understood as a value used for grouping or binning acquired information (e.g., data acquired from the CT detector 114) into high and low voltage groups or bins. In the depicted embodiment, portions of acquired data acquired above the voltage threshold 220 are grouped as high energy data and portions of the acquired data acquired below the voltage threshold 220 are grouped as low energy data. The use of data acquired at different voltage levels may allow for improved material density determinations, for example. In the illustrated embodiment, the voltage threshold 220 is at 110 kV, or halfway between the high energy 202 and the low energy 204. The voltage threshold 220 may be adjusted to provide improved imaging based on clinical task, patient size, and/or scan parameters.

Figure 3:
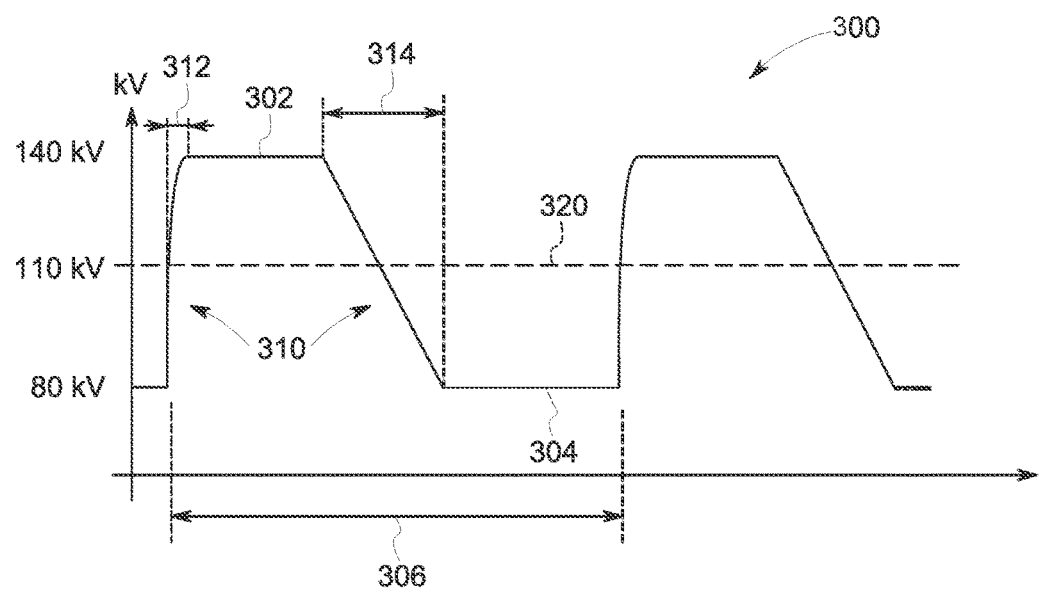
FIG. 3 illustrates an example waveform configuration having a different fall time than the waveform configuration of FIG. 2, in accordance with various embodiments.

FIG. 3 illustrates an additional example of a waveform configuration 300 formed in accordance with various embodiments. Similar to the waveform configuration 200, the waveform configuration 300 alternates between a high energy 302 (corresponding to 140 kV in the illustrated embodiment) and a low energy 304 (corresponding to 80 kV) over a period 306. Further, the waveform configuration 300 also includes a transition configuration 310, which in turn includes a rise time 312 and a fall time 314. It may be noted that while the rise time 312 of FIG. 3 is similar to that of FIG. 2, the fall time 314 of FIG. 3 is longer than that of FIG. 2, resulting in the portion of the waveform configuration 300 during the fall time 314 having a flatter slope than the corresponding portion of the waveform configuration 200 of FIG. 2.

The waveform configuration 300 also includes a voltage threshold 320. Similar to the embodiment depicted in FIG. 2, the voltage threshold 320 is at 110 kV, or halfway between the high energy 302 and the low energy 304. Again, the voltage threshold 320 may be adjusted to provide improved imaging based on clinical task, patient size, and/or scan parameters.

It may be noted that changing the voltage threshold 220, 320 does not change the shape of the waveform, but instead relates to the binning or grouping of information acquired using an X-ray source (e.g., X-ray source 112) operated with the waveform. Adjusting the voltage threshold 220, 320 may not impact overall dose. Changing voltage threshold 220, 320, however, does impact effective low voltage, effective high voltage, and voltage separation.

Figure 4:
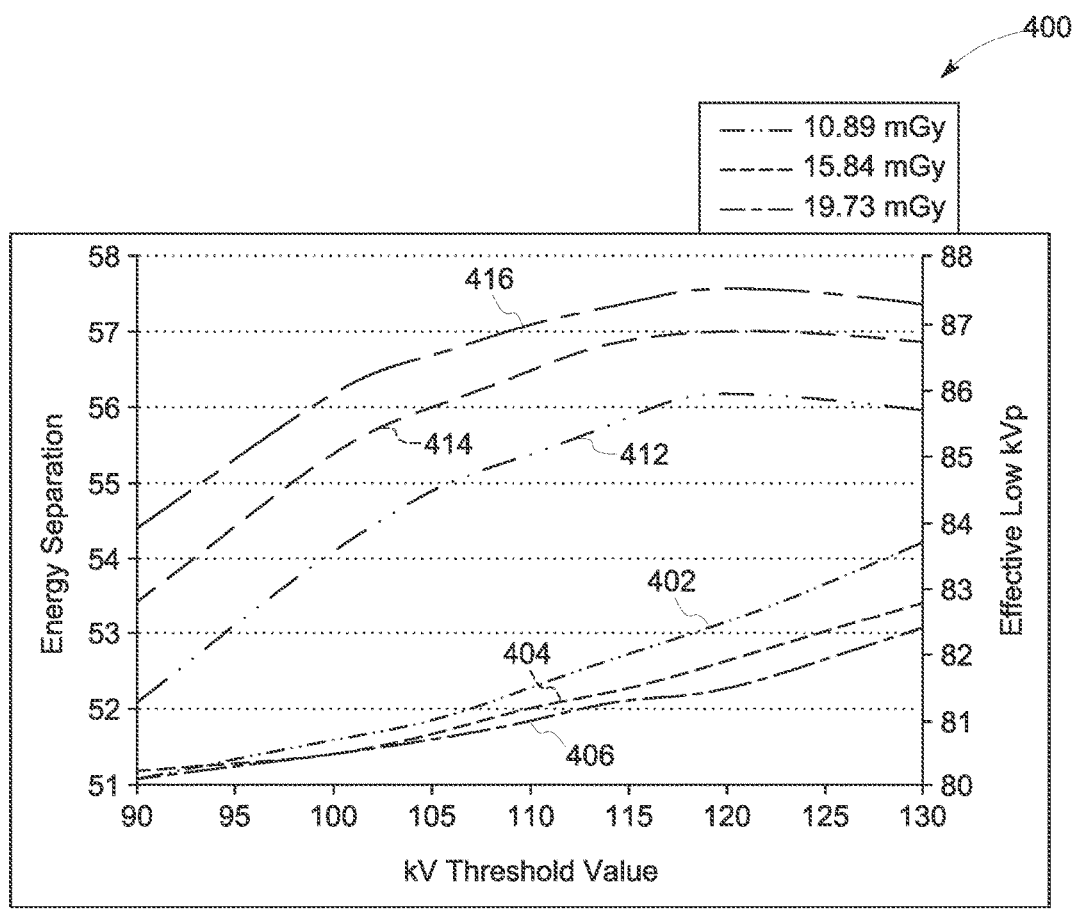
FIG. 4 illustrates a plot of effective low voltage and energy separation against voltage threshold in accordance with various embodiments.

FIG. 4 illustrates an example graph 400 depicting the effects of changing voltage threshold for one embodiment. It may be noted that the particular values and shapes of curves are provided by way of example for illustrative purposes, and may vary for different embodiments or applications. The graph 400 includes dashed curves 402, 404, 406 corresponding to effective low voltage values plotted against voltage thresholds, and solid curves 412, 414, and 416 corresponding to energy separation plotted against voltage thresholds. In the illustrated embodiment, the nominal low voltage level is 80 kVp. As seen in FIG. 4, as the voltage threshold (horizontal axis) increases, the value of effective low voltage (values on vertical axis on right side of graph 400) increases. As also seen in FIG. 4, as the voltage threshold increases, the amount of energy separation (values on vertical axis on left side of graph 400) increases, up to around 115-120 kVp, after which point the energy separation decreases. Thus, for the illustrated embodiment, for an application where effective low voltage is desired to be increased, the voltage threshold may be increased until the desired effective low voltage is achieved. For an application where it is desired to maximize energy separation, the voltage threshold may be set between about 115-120 kV.

Accordingly, the voltage threshold 220, 320 may be adjusted or otherwise controlled to provide improved imaging in various embodiments. For example, increasing the voltage threshold 220, 320 may increase the effective low voltage and the effective high voltage to increase as well. This increase may, for example, benefit large patient scanning by balancing the flux between the high voltage and the low voltage. As changing the voltage threshold 220, 320 does not change patient dose, scans at higher voltage thresholds may be acquired without having to scan at relatively higher currents and/or reaching tube power limitations. As another example, decreasing the voltage threshold 220, 320 may cause the effective low voltage and the effective high voltage levels to decrease, providing contrast improvement. Accordingly, for applications where improved flux (e.g., for large patients) is desired, the voltage threshold 220, 320 may be increased, whereas for applications where contrast improvement is more highly desired, the voltage threshold 220, 320 may be decreased.

Alternatively or additionally, the transition time configuration 210, 310 (including the rise time and/or fall time, and/or shape of waveform during one or more of the rise time or fall time) may be adjusted or otherwise controlled to provide improved imaging in various embodiments. For example, adjusting rise time and fall time may affect flux as well as energy separation between the low energy and the high energy or voltage levels.

It may be noted that decreasing the fall time and/or the rise time (or increasing the slope of the portion of the waveform configuration 200, 300 during the fall time and/or the rise time) may increase the energy separation between low and high voltages or energies. Such an increase in energy separation may benefit normal size patient spectral imaging, for example by improving material density accuracy. On the other hand, increasing the fall time and/or the rise time (or decreasing the slope of the portion of the waveform configuration 200, 300 during the fall time and/or the rise time) may help balance the flux between effective high and low energy levels, which may be benefit smaller patients.

Figure 5:
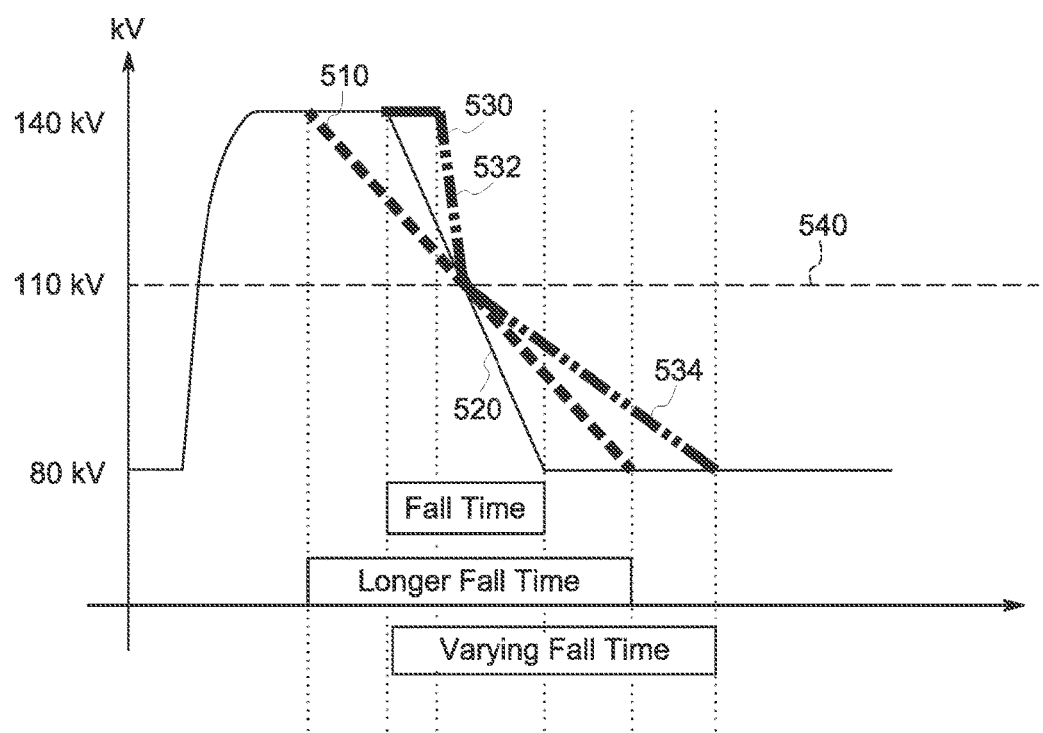
FIG. 5 illustrates example fall time configurations in accordance with various embodiments.

In some embodiments, the transition time configuration may include a first slope during a first portion of the fall time and a second slope during a second portion of the fall time, with the first slope and the second slope being different. FIG. 5 illustrates example fall time configurations in accordance with various embodiments. As seen in FIG. 5, fall time configuration 510 is generally straight and continuous and has a relatively flat slope. Fall time configuration 520 is also generally straight and continuous, but has relatively steep slope. Fall time configuration 530 includes a first portion 532 that has a steep slope and a second portion 534 that has a flatter slope. The first portion 532 is above a voltage threshold 540, and the second portion 534 is below the voltage threshold 540. Accordingly, the shape of the fall time waveform configuration may be tailored for each energy or voltage level. For example, the first portion 532 provides for a higher effective voltage than the fall time configuration 510 or 520, while the second portion 534 provides for increasing effective low voltage and increased flux.

It may be noted that a duty cycle for the waveform configuration may also be adjusted or otherwise controlled in various embodiments. As used herein, a duty cycle may be understood as the percentage of time in which acquired detector data is binned to a low energy portion of the acquisition compared to the total time the detector data is binned to both high and lower energy in spectral imaging. For example, as decreasing the duty cycle increases dose and amount of time spent at the high voltage level, increasing the duty cycle may benefit imaging of larger patients. On the other hand, increasing the duty cycle will decrease the patient dose and may benefit smaller patients. It may be noted that, at higher duty cycles, the flux at the low energy is decreased and will decrease both effective high and low voltages.

Figure 6:
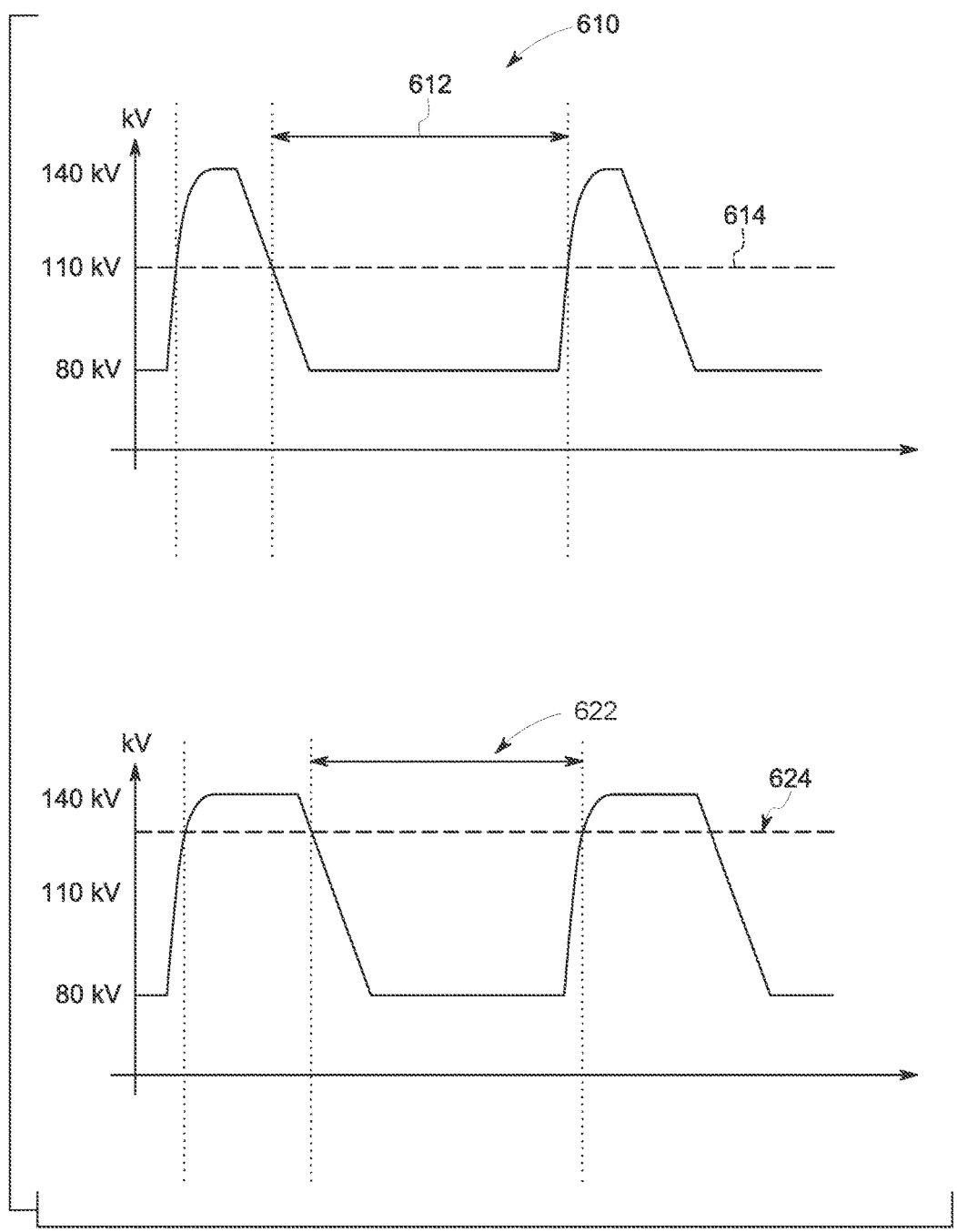
FIG. 6 illustrates an example of adjusting a waveform configuration in accordance with various embodiments.

By adjusting two or more of voltage threshold, rise/fall time, and duty cycle together, desired effective high and low voltages along with desired flux levels may be achieved. For example, FIG. 6 depicts example waveform configurations in accordance with various embodiments. As seen in FIG. 6, a first waveform configuration 610 has a duty cycle 612 and a voltage threshold 614, while a second waveform configuration 620 has a duty cycle 622 and a voltage threshold 624. The duty cycle 622 is decreased relative to the duty cycle 612, whereas the voltage threshold 624 is higher than the voltage threshold 614. By decreasing the duty cycle of the second waveform configuration 620 relative to the first waveform configuration 610 while increasing the voltage threshold of the second waveform configuration 620 relative to the first waveform configuration 610, the second waveform configuration 620 provides improved scanning for large patients.

Returning to FIG. 1, the processing unit 120 is also configured to implement the waveform configuration on the CT acquisition unit 110. For example, the processing unit 120 may implement the waveform configuration by autonomously adjusting a previous setting (e.g., autonomously adjusting from a setting for a different patient or procedure, or from a default setting). It may be noted that the waveform configuration may be adjusted only at the beginning of a scan and left the same during the scan in some embodiments, while the waveform configuration may be adjusted during a scan in other embodiments. For example, in some embodiments, the processing unit 120 may be configured to determine and implement different waveform configurations for different rotational positions of the CT acquisition unit 110 as the CT acquisition unit 110 rotates about the object to be imaged. For example, an object may appear larger in a first group of views (e.g., a side view) than from a second group of views (e.g., a top view) so a waveform configuration tailored for better penetration of highly attenuating tissue may be used for the first group of views and a different waveform configuration used for the second group of views.

The processing unit 120 is also configured to control the CT acquisition unit 110 to perform an imaging scan using the determined waveform configuration. In some embodiments, the processing unit 120 is also configured to reconstruct an image using information acquired during the imaging scan.

In the illustrated embodiment, the processing unit 120 includes a reconstruction module 122, a determination module 124, a control module 126, and a memory 128. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein. It may be noted that the memory 128 may include one or more databases, lookup tables, or other sources of stored information utilized to determine appropriate CT acquisition waveform configurations based on patient size, clinical task, and/or scan parameters. It may further be noted that the memory 128 may have stored thereon instructions for directing the processing unit 120 to perform one or more aspects of the methods, steps, or processes discussed herein.

The depicted reconstruction module 122 is configured to reconstruct one or more images using imaging or projection data acquired from the CT detector 114. For example, the reconstruction module 122 may receive imaging information from the CT detector 114 taken over a number of views (e.g., for a full rotation or portion thereof, or for a number of rotations taken at different positions along the length of an object to be imaged) and reconstruct an image used for diagnostic purposes.

In the illustrated embodiment, the determination module 124 is configured to determine one or more waveform configurations as discussed herein for the X-ray source 112 based on at least one of a patient size, clinical task or scan parameters. In some embodiments, the determination module 124 may access a database and/or lookup table stored on the memory 128 that correlates optimal or improved waveform configurations with combinations of patient sizes, clinical tasks, and/or scan parameters.

In various embodiments, the determination module 124 may be communicably coupled to the control module 126, with the control module 126 configured to control the CT acquisition unit 110 and/or other aspects of the system 100 to perform the imaging scans using one or more waveform configurations for the CT acquisition unit 110 called for by the determination module 124. For example, the X-ray source 112 may be controlled to switch between a high energy level and a low energy level over a fall time and duty cycle specified by the determination module 124, and may utilize a voltage threshold specified by the determination module to bin acquired data.

The output unit 140 is configured to provide information to the user. The output unit 140 may be configured to display, for example, a reconstructed image or, as another example, may display a selected or determined waveform configuration for adjustment and/or approval by an operator before implementing the determined waveform configuration. The output unit 140 may include one or more of a screen, a touchscreen, a printer, or the like.

The input unit 150 may be configured to obtain an input that corresponds to one or more settings or characteristics of a scan to be performed, and to provide the input (or information corresponding to the input) to the processing unit 120, which may use the input to determine the waveform configuration. The input may include, for example, a clinical task (e.g., diagnose kidney stones) and/or portion of the body to be scanned (e.g., head, body). The input unit 150 may be configured to accept a manual user input, such as via a touchscreen, keyboard, mouse, or the like. Additionally or alternatively, the input unit 150 may receive information from another aspect of the imaging system 100, another system, or a remote computer, for example, via a port or other connectivity device. The input unit 150 may also be configured to obtain user approval or denial of a proposed scanning setting.

Figure 7:
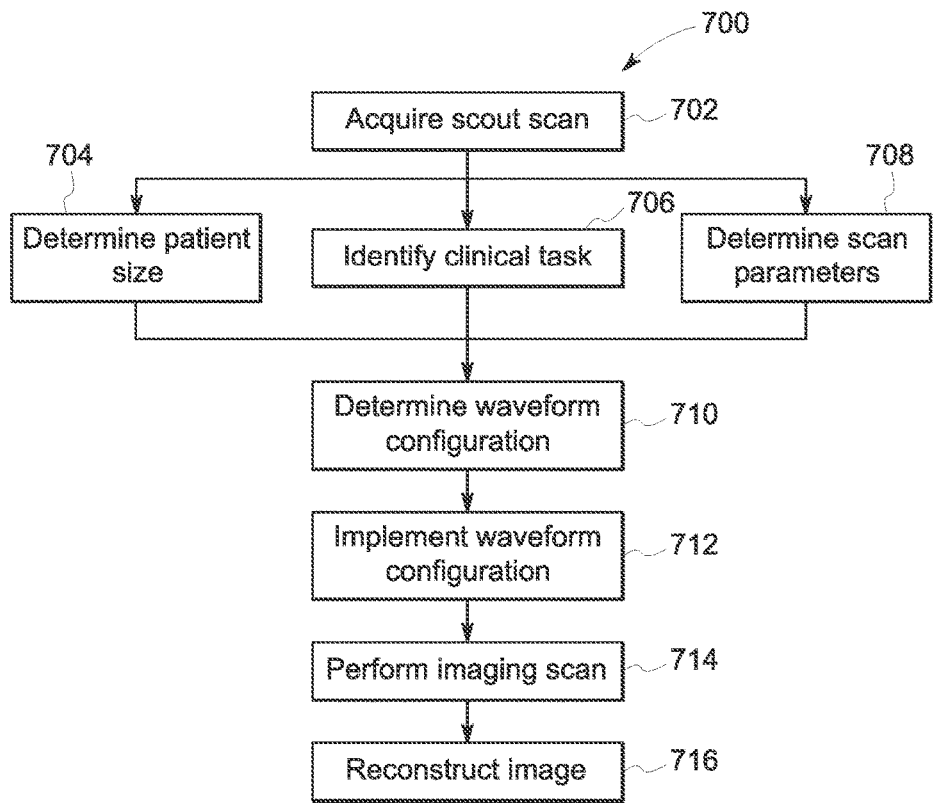
FIG. 7 is a flowchart of a method in accordance with various embodiments.

FIG. 7 provides a flowchart of a method 700 for imaging an object using dual-energy scanning, in accordance with various embodiments. The method 700, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 700 may be able to be used as one or more algorithms to direct hardware (e.g., one or more aspects of the processing unit 120) to perform one or more operations described herein.

At 702, a scout scan is acquired. In some embodiments, at least 2 scout scans may be acquired. In some embodiments, a helical scout scan may be acquired. The scout scan may be acquired to plan scanning of a patient. For example, a scout scan may be utilized to identify the location of organs and/or regions of interest of the patient, for example to determine how much of the patient is to be scanned for a particular clinical or diagnostic task. The scout scan may also be used to determine a patient size and/or attenuation level. A gantry may be stationary during acquisition of the scout scan.

At 704, the patient size is determined, for example using the scout scan. At 706, a clinical task to be performed is identified, for example, using information provided by an operator or obtained from a database. At 708, scan parameters (e.g., scan field of view, rotation time, collimation) are determined. The scan parameters may be determined, for example, based at least in part on the clinical task.

At 710, a waveform configuration is determined for use with a CT acquisition unit to acquire imaging information. The waveform configuration may be determined based on at least one of a patient size, clinical task, or scan parameters. As discussed herein, the waveform configuration includes at least one of a transition configuration (e.g., rise time, fall time, slope of waveform during all or a portion of a rise and/or fall time) or a voltage threshold.

At 712, the waveform configuration is implemented on the CT acquisition unit. For example, the waveform configuration may be implemented by autonomously switching from a previous waveform configuration to the waveform configuration determined at 710. In some embodiments, different waveform configurations may be determined and implemented for different rotational positions of the CT acquisition unit.

At 714, the CT acquisition unit is controlled to perform an imaging scan using the determined waveform configuration. In the illustrated embodiment, an X-ray source and detector may be rotated about the object being imaged and operated in a manner prescribed by the waveform configuration to collect imaging information at the detector. For example, the voltage level of the X-ray source may be switched as directed by the waveform configuration, and acquired data may be binned as directed by the voltage threshold of the waveform configuration. Imaging or projection data or information is obtained via the detector during the performance of the scan. At 716, an image is reconstructed using information acquired during the imaging scan.

Figure 8:
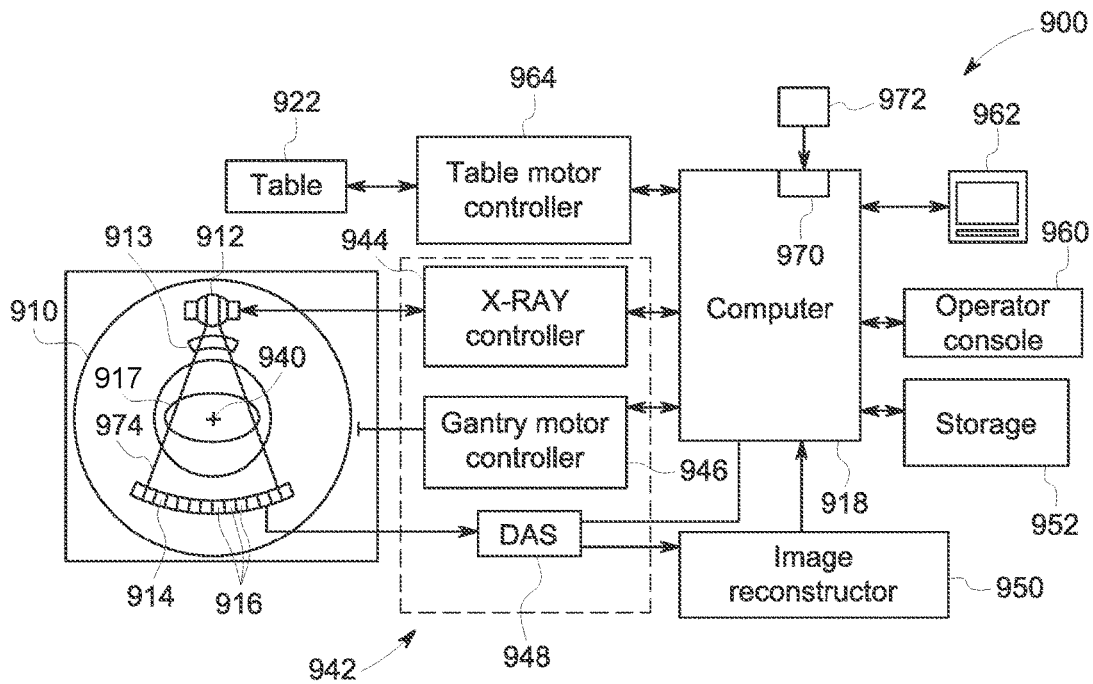
FIG. 8 is a schematic block diagram of an imaging system in accordance with various embodiments.

Various methods and/or systems (and/or aspects thereof) described herein may be implemented using a medical imaging system. For example, FIG. 8 is a block schematic diagram of an exemplary CT imaging system 900 that may be utilized to implement various embodiments discussed herein. Although the CT imaging system 900 is illustrated as a standalone imaging system, it should be noted that the CT imaging system 900 may form part of a multi-modality imaging system in some embodiments. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter module are provided proximate the X-ray source 912. In various embodiments, the source collimator 913 may be configured to provide wide collimation as discussed herein. The detector array 914 includes a plurality of detector elements 916 that are arranged in rows and channels that together sense the projected X-rays that pass through a subject. The CT imaging system 900 also includes a computer 918 that receives the projection data from the detector array 914 and processes the projection data to reconstruct an image of the subject. The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject into and out of the gantry 910. Particularly, the motorized table 922 moves at least a portion of the subject through a gantry opening (not shown) that extends through the gantry 910. Further, the motorized table 922 may be used to move the subject vertically within the bore of the gantry 910.

The depicted detector array 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 8 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from the computer 918. It may be noted that one or more of the computer 918, controllers, or the like may be incorporated as part of a processing unit such as the processing unit 120 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject in the gantry 910. Particularly, the motorized table 922 moves at least a portion of the subject through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view" or "projection." A "scan" of the subject 917 comprises a set of views made at different gantry angles, or view angles, during one or more revolutions of the X-ray source 912 and the detector array 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An imaging system comprising:
a computed tomography (CT) acquisition unit comprising an X-ray source and a CT detector configured to collect CT imaging data of an object to be imaged, the X-ray source and the CT detector configured to be rotated about the object to be imaged and to collect a series of projections of the object as the X-ray source and the CT detector rotate about the object to be imaged, the X-ray source configured to be switched between a high voltage and a low voltage during collection of the series of projections; and
a processing unit comprising at least one processor operably coupled to the CT acquisition unit, the processing unit configured to:
determine a voltage delivery configuration for the X-ray source based on at least one of a patient size, a clinical task, or scan parameters, the voltage delivery configuration comprising a voltage threshold, wherein all portions of acquired data from the series of projections acquired above the voltage threshold are grouped as high energy data and all portions of the acquired data from the series of projections acquired below the voltage threshold are grouped as low energy data;
implement the voltage delivery configuration on the CT acquisition unit; and
control the CT acquisition unit to perform an imaging scan using the determined voltage delivery configuration.

2. The imaging system of claim 1, wherein the processing unit is further configured to reconstruct an image using information acquired with the series of projections during the imaging scan.

3. The imaging system of claim 1, wherein the processing unit, configured to implement the voltage delivery configuration, is further configured to autonomously switch from a previous voltage delivery configuration to the determined voltage delivery configuration.

4. The imaging system of claim 1, wherein the processing unit is further configured to determine and implement different voltage delivery configurations for different rotational positions of the CT acquisition unit as the CT acquisition unit rotates about the object to be imaged.

5. The imaging system of claim 1, wherein the voltage delivery configuration further comprises a duty cycle, wherein the processing unit is further configured to determine the duty cycle based on at least one of the patient size, the clinical task, or the scan parameters.

6. The imaging system of claim 1, wherein the voltage delivery configuration comprises a transition configuration corresponding to a transition between the high voltage and the low voltage of the X-ray source.

7. The imaging system of claim 6, wherein the transition configuration comprises a rise time from the low voltage to the high voltage and a fall time from the high voltage to the low voltage.

8. The imaging system of claim 7, wherein the transition configuration comprises a first slope during a first portion of the fall time and a second slope during a second portion of the fall time, wherein the first slope and the second slope are different.

9. The imaging system of claim 8, wherein the first portion of the fall time is above the voltage threshold and the second portion of the fall time is below the voltage threshold.

10. A method comprising:
  determining, with at least one processor, a voltage delivery configuration for an X-ray source of a computed tomography (CT) acquisition unit based on at least one of a patient size, a clinical task, or scan parameters, the voltage delivery configuration comprising a voltage threshold, wherein all portions of acquired data acquired above the voltage threshold are grouped as high energy data and all portions of the acquired data acquired below the voltage threshold are grouped as low energy data;
  implementing the voltage delivery configuration on the CT acquisition unit; and
  controlling the CT acquisition unit to perform an imaging scan using the determined voltage delivery configuration.

11. The method of claim 10, further comprising reconstructing an image using the acquired data acquired during the imaging scan.

12. The method of claim 10, wherein the transition configuration comprises a rise time from the low voltage to the high voltage and a fall time from the high voltage to the low voltage.

13. The method of claim 12, wherein the transition configuration comprises a first slope during a first portion of the fall time and a second slope during a second portion of the fall time, wherein the first slope and the second slope are different.

14. The method of claim 13, wherein the first portion of the fall time is above the voltage threshold and the second portion of the fall time is below the voltage threshold.

15. The method of claim 10, wherein implementing the voltage delivery configuration comprises autonomously switching from a previous voltage delivery configuration to the determined voltage delivery configuration.

16. The method of claim 10, further comprising determining and implementing different voltage delivery configurations for different rotational positions of the CT acquisition unit as the CT acquisition unit rotates about an object to be imaged.

17. The method of claim 10, wherein the voltage delivery configuration further comprises a duty cycle.

18. The method of claim 10, wherein the voltage delivery configuration comprises a transition configuration corresponding to a transition between the high voltage and the low voltage of the X-ray source.

19. A tangible and non-transitory computer readable medium comprising one or more computer software modules configured to direct one or more processors to:
  determine a voltage delivery configuration for an X-ray source of a computed tomography (CT) acquisition unit based on at least one of a patient size, a clinical task, or scan parameters, the voltage delivery configuration comprising a voltage threshold, wherein all portions of acquired data acquired above the voltage threshold are grouped as high energy data and all portions of the acquired data acquired below the voltage threshold are grouped as low energy data;
  implement the voltage delivery configuration on the CT acquisition unit; and
  control the CT acquisition unit to perform an imaging scan using the determined voltage delivery configuration.

20. The tangible and non-transitory computer readable medium of claim 19, wherein the transition time configuration comprises a rise time from the low voltage to the high voltage and a fall time from the high voltage to the low voltage, and wherein the transition time configuration comprises a first slope during a first portion of the fall time and a second slope during a second portion of the fall time, wherein the first slope and the second slope are different.

21. The tangible and non-transitory computer readable medium of claim 19, wherein the one or more computer software modules are further configured to direct the one or more processors to implement autonomously switching from a previous voltage delivery configuration to the determined voltage delivery configuration.

22. The tangible and non-transitory computer readable medium of claim 19, wherein the one or more computer software modules are further configured to direct the one or more processors to determine and implement different voltage delivery configurations for different rotational positions of the CT acquisition unit as the CT acquisition unit rotates about an object to be imaged.

23. The tangible and non-transitory computer readable medium of claim 19, wherein the voltage delivery configuration comprises a transition configuration corresponding to a transition between the high voltage and the low voltage of the X-ray source.

24. An imaging system comprising:
  a computed tomography (CT) acquisition unit comprising an X-ray source and a CT detector configured to collect CT imaging data of an object to be imaged, the X-ray source and the CT detector configured to be rotated about the object to be imaged and to collect a series of projections of the object as the X-ray source and the CT detector rotate about the object to be imaged, the X-ray source configured to be switched between a high voltage and a low voltage during collection of the series of projections; and
  a processing unit comprising at least one processor operably coupled to the CT acquisition unit, the processing unit configured to:
    determine a voltage delivery configuration for the X-ray source based on at least one of a patient size, a clinical task, or scan parameters, the voltage delivery configuration comprising at least one of a transition configuration or a voltage threshold, wherein the transition configuration corresponds to a transition between the high voltage and the low voltage of the X-ray source, wherein all portions of acquired data from the series of projections acquired above the voltage threshold are grouped as high energy data and all portions of the acquired data from the series of projections acquired below the voltage threshold are grouped as low energy data;
    implement the voltage delivery configuration on the CT acquisition unit, wherein the processing unit is further configured to determine and implement different voltage delivery configurations for different rotational positions of the CT acquisition unit as the CT acquisition unit rotates about the object to be imaged; and
    control the CT acquisition unit to perform an imaging scan using the determined voltage delivery configuration.

25. An imaging system comprising:
  a computed tomography (CT) acquisition unit comprising an X-ray source and a CT detector configured to collect CT imaging data of an object to be imaged, the X-ray source and the CT detector configured to be rotated about the object to be imaged and to collect a series of projections of the object as the X-ray source and the CT detector rotate about the object to be imaged, the X-ray source configured to be switched between a high voltage and a low voltage during collection of the series of projections; and a processing unit comprising at least one processor operably coupled to the CT acquisition unit, the processing unit configured to:

determine a voltage delivery configuration for the X-ray source based on at least one of a patient size, a clinical task, or scan parameters, the voltage delivery configuration comprising at least one of a transition configuration or a voltage threshold, wherein the transition configuration corresponds to a transition between the high voltage and the low voltage of the X-ray source, wherein portions of acquired data from the series of projections acquired above the voltage threshold are grouped as high energy data and portions of the acquired data from the series of projections acquired below the voltage threshold are grouped as low energy data, wherein the voltage delivery configuration further comprises a duty cycle, wherein the processing unit is further configured to determine the duty cycle based on at least one of the patient size, the clinical task, or the scan parameters;

implement the voltage delivery configuration on the CT acquisition unit; and control the CT acquisition unit to perform an imaging scan using the determined voltage delivery configuration.

* * * * *